United States Patent [19]

Sikorski et al.

[11] 4,445,929

[45] May 1, 1984

[54] HERBICIDAL ESTER DERIVATIVES OF N-ALKYLTHIO AND N-CYCLOALKYLTHIO-N-PHOSPHONOMETHYLGLYCINONITRILE

[75] Inventors: James A. Sikorski, West Lafayette, Ind.; Mary A. Hoobler, Creve Coeur, Mo.

[73] Assignee: Monsanto Company, St. Louis, Mo.

[21] Appl. No.: 309,325

[22] Filed: Oct. 5, 1981

[51] Int. Cl.³ ......................... A01N 57/22; C07F 9/40
[52] U.S. Cl. ........................................ 71/087; 260/940
[58] Field of Search ............................ 260/940; 71/87

[56] References Cited

U.S. PATENT DOCUMENTS 4,008,296  2/1977  Barton ..................................... 71/86
4,067,719  1/1978  Dutra ...................................... 71/86
4,252,554  2/1981  Dutra et al. ............................. 71/87

OTHER PUBLICATIONS

Unvarified Translation of Japanese Pat. No. 14,2,047 of 5/1976.

*Primary Examiner*—Anton H. Sutto
*Attorney, Agent, or Firm*—Raymond C. Loyer; Gordon F. Sieckmann; Richard H. Shear

[57] ABSTRACT

This disclosure relates to novel ester derivatives of N-alkylthio and N-cycloalkylthio-N-phosphonomethylglycinonitrile which are useful as herbicides and to a process for producing the same. This disclosure further relates to herbicidal compositions containing such N-phosphonomethylglycinonitrile derivatives and to herbicidal methods employing such compounds and compositions.

21 Claims, No Drawings

HERBICIDAL ESTER DERIVATIVES OF N-ALKYLTHIO AND N-CYCLOALKYLTHIO-N-PHOSPHONOMETHYL-GLYCINONITRILE

This invention relates to novel ester derivatives of N-alkylthio and N-cycloalkylthio-N-phosphonomethylglycinonitrile which are useful as herbicides and to a process for preparing the same. This invention further relates to herbicidal compositions containing such N-phosphonomethylglycinonitriles and to herbicidal methods employing such compounds and compositions.

U.S. Pat. No. 4,067,719 discloses N-phosphonomethylglycinonitriles of the formula

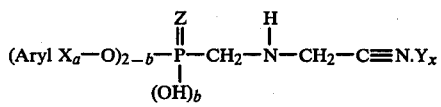

wherein (Aryl) is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, a is an integer from zero to 3, b is an integer from zero to 1, Y is a strong acid capable of forming a salt with the amino group, and x is zero or 1, provided that x must be zero when b is 1, as well as a process for producing such compounds. These N-phosphonomethylglycinonitriles are useful as herbicides.

U.S. Pat. No. 4,008,296 describes ester derivatives of N-phosphonomethylglycinonitrile having the formula

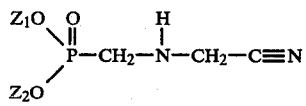

wherein $Z_1$ and $Z_2$ each represent an alkyl radical of from 1 to 6 carbon atoms; which are useful as herbicides.

Japanese L.O.P. No. 142047/1977 discloses phenylcyanomethylaminomethylphosphonates of the formula

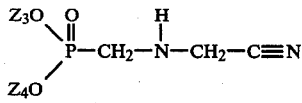

wherein $Z_3$ is hydrogen or phenyl and $Z_4$ is phenyl. Japanese L.O.P. No. 93323/1974 describes the preparation of N-(diethylphosphonomethyl)aminoacetonitrile.

U.S. Pat. No. 4,252,554 issued to Gerard A. Dutra et al on Feb. 24, 1981 discloses compounds represented by the formula

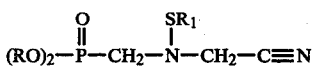

wherein R is phenyl, naphthyl or biphenylyl or phenyl, naphthyl or biphenylyl substituted with from 1 to 3 substituents independently selected from the group consisting of lower alkyl, lower alkoxy, lower alkylthio, lower alkoxycarbonyl, methylenedioxy, trifluoromethyl, cyano, nitro and halogen; and $R_1$ is phenyl or phenyl substituted with from 1 to 3 substituents independently selected from the group consisting of lower alkyl, lower alkoxy, halogen, trifluoromethyl and nitro.

The compounds of the present invention are represented by the formula

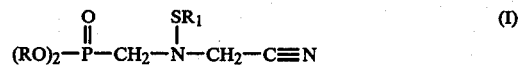

wherein R is phenyl, naphthyl or biphenylyl or phenyl, naphthyl or biphenylyl substituted with from one to three substituents independently selected from the class consisting of lower alkyl, lower alkoxy, lower alkylthio, alkoxycarbonyl, methylenedioxy, trifluoromethyl, cyano, nitro and halogen; and $R_1$ is alkyl or cycloalkyl.

It is preferred that R is phenyl, and $R_1$ is methyl, ethyl, isopropyl, nebutyl and cyclohexyl.

As employed herein, the term "lower alkyl" designates alkyl radicals which have one to four carbon atoms in a straight or branched chain, such as, for example, methyl, ethyl, propyl, isopropyl, butyl, isobutyl, sec-butyl, and t-butyl.

The term "alkyl" designates these alkyl radicals which have one to 8 carbon atoms in a straight or branched chain.

The term "halo or halogen" as employed herein means chlorine, bromine, iodine and fluorine.

The term "lower alkoxy" includes groups representative of the term "lower alkyl" in combination with oxygen and includes methoxy, ethoxy, propoxy, butoxy mixtures thereof and the like.

The term "lower alkylthio" includes representatives of lower alkyl in combination with sulfur.

The term "lower alkoxycarbonyl" includes groups representative of the aforedefined term "lower alkoxy" in combinaton with a carbonyl group.

The term "cycloalkyl" is employed herein to represent carbon-hydrogen atoms arranged in a cyclic or ring arrangement having 3 to 8 carbon atoms in the ring arrangement. Typical groups representative of cycloalkyl include cyclopentyl, cyclohexyl and the like.

Illustrative of the substituted phenyl groups which R independently represents are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri- substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl groups represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methylbiphenylyl, nitrobiphenylyl, bromobiphenylyl, dimethylbiphenylyl, difluorobiphenylyl, trimethylbiphenylyl and the like.

In accordance with the present invention, the N-alkylthio-N-phosphonomethylglycinonitriles of formula (I) are prepared by reacting a compound of the formula

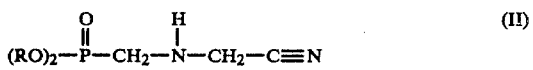

wherein R is above defined; in an aprotic solvent, with a sulfenyl chloride of the formula $$R_1—S—Cl \qquad (III)$$

wherein $R_1$ is above defined; in the presence of a hydrogen chloride acceptor.

Typical sulfenyl chlorides which may be employed include those prepared by a method described in Synthesis 9, 690 (1980), and other references described therein, which are incorporated herein in their entirety by reference.

It has been found that the reaction temperature may range from −40° to 100° C. For ease of reaction and recovery of product, it is preferred to conduct the process of the present invention within a range of −40° to 30° C.

In preparing the novel N-phosphonomethyl glycinonitrile derivatives of formula (I), the ratio of reactants is not narrowly critical. For best results, however, for each mole of a compound of formula (II), one should employ one mole of a sulfenyl chloride of formula (III) to produce one mole of a glycinonitrile compound of formula (I). It is preferred to employ an excess of a sulfenyl chloride of formula (III) for ease of reaction and maximum yield of product. The hydrogen chloride acceptor is preferably used in stoichiometric excess to insure completeness of reaction.

The hydrogen chloride acceptor is an amine, preferably a tertiary amine, which will not react with the reactants or products formed. Examples of tertiary amine hydrogen chloride acceptors include trimethylamine, triethylamine, tributylamine, trihexylamine, 1,5-diazabicyclo[5.4.0]-undec-5-ene, pyridine, quinoline and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, methylene chloride, tetrahydrofuran, cyclohexane, methylcyclohexane, hexane, octane, dioxane, ethyl ether and the like, although a solvent is not required.

While the process of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate to those skilled in the art the manner in which specific compounds within the scope of this invention can be prepared. In the examples, all parts are parts by weight unless otherwise expressly stated.

General Procedure for the Preparation of Alkyl and Cycloalkyl Sulfenamide Derivatives of N-Phosphonomethylglycinonitriles for

EXAMPLES I-V

An oven-dried flask cooled under nitrogen was charged with the appropriate alkyl or cycloalkyldisulfide (about 0.03–0.04 mole) and methylene chloride and cooled to −40° C. in a dry ice-acetonitrile bath. Sulfuryl chloride (one equivalent) (either neat or as a solution in methylene chloride) was added slowly via syringe or cannula, maintaining the temperature below −30° C. An immediate yellow color indicated formation of an intermediate sulfenyl chloride of formula (III) (two equivalents). This reaction mixture was stirred at −40° C. for 15–30 min. and transferred via cannula to a solution of the appropriate N-phosphonomethylglycinonitrile derivative of formula (II) (about 0.03 to about 0.05 mole) and excess triethylamine in methylene chloride at −40° C. Generally, an excess of the sulfenyl chloride was employed. The yellow reaction mixture was stirred overnight after allowing to warm slowly to room temperature. The reaction mixture was washed with cold 10% aqueous NaOH followed by cold water, dried over MgSO4, filtered and concentrated in vacuo. Purification by HPLC (except for example II which was purified by gravity column) on a Waters Prep Pak 500 silica gel column eluting with 10–50% ethyl acetate/cyclohexane gave the desired sulfenamides of formula (I). $^1$H NMR, $^{31}$P NMR and elemental analyses were consistent with pure product.

EXAMPLE I

Phosphonic acid, (((cyanomethyl)methylthio)amino)methyl)-, diphenyl ester was prepared corresponding to a compound of formula (I) wherein R is phenyl and $R_1$ is methyl, as a yellow solid having a melting point of 52°–54° C. and an analysis: $C_{16}H_{17}N_2O_3PS$: Calcd: C, 55.17; H, 4.92; N, 8.04; S, 9.20. Found: C, 55.23; H, 4.93; N, 8.01; S, 9.19.

EXAMPLE II

Phosphonic acid, (((cyanomethyl)ethylthio)amino)methyl)-, diphenyl ester was prepared corresponding to a compound of formula (I) wherein R is phenyl and $R_1$ is ethyl, as a light yellow solid, having a melting point of 51°–54° C. and an analysis: $C_{17}H_{19}N_2O_3PS$: Calcd: C, 56.35; H, 5.29; N, 7.73; S, 8.85. Found: C, 56.36; H, 5.28; N, 7.69; S, 8.84.

EXAMPLE III

Phosphonic acid, (((cyanomethyl)isopropylthio)amino)methyl)-, diphenyl ester was prepared corresponding to a compound of formula (I) wherein R is phenyl and $R_1$ is isopropyl as a brown solid having a melting point of 58°–61° C. and having an analysis: $C_{18}H_{21}N_2O_3PS$: Calcd: C, 57.44; H, 5.62; N, 7.44; S, 8.52. Found: C, 57.22; H, 5.66; N, 7.32; S, 8.42.

EXAMPLE IV

Phosphonic acid, (((cyanomethyl)(cyclohexylthio)amino)methyl)-, diphenyl ester was prepared corresponding to a compound of formula (I) wherein R is phenyl and $R_1$ is cyclohexyl as a tan solid, having a melting point of 66°–68° C. and an analysis $C_{21}H_{25}N_2O_3PS$: Calcd: C, 60.56; H, 6.05; N, 6.73; S, 7.70. Found: C, 60.46; H, 6.11; N, 6.63; S, 7.75.

EXAMPLE V

Phosphonic acid (((cyanomethyl)(n-butylthio)amino)methyl)-diphenyl ester was prepared corresponding to a compound of formula (I) wherein R is phenyl and $R_1$ is n-butyl as a yellow solid having a melting point of 32°–34° C. and an analysis $C_{19}H_{23}N_2O_3PS$: Calcd: C, 58.45; H, 5.94; N, 7.17; S, 8.21. Found: C, 58.23; H, 6.01; N, 7.09; S, 8.12.

EXAMPLE VI

The post emergence herbicidal activity of some of the various compounds of this invention was demonstrated by a greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution of suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A — Canada Thistle* | K — Barnyardgrass |
| B — Cocklebur | L — Soybean |
| C — Velvetleaf | M — Sugar Beet |
| D — Morningglory | N — Wheat |
| E — Lambsquarters | O — Rice |
| F — Smartweed | P — Sorghum |
| G — Yellow Nutsedge* | Q — Wild Buckwheat |
| H — Quackgrass* | R — Hemp Sesbania |
| I — Johnsongrass* | S — Panicum Spp |
| J — Downy Brome | T — Crabgrass |

*Established from vegetative propagules.

A dash (-) in the tables indicates that the particular species was absent in the test.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| I | 4 | 56.0 | 4 | 4 | 3 | 4 | 4 | 4 | 3 | 4 | 3 | 4 | 3 |
|   | 4 | 11.2 | 4 | 4 | 3 | 4 | 4 | 3 | 2 | 2 | 1 | 3 | 4 |
|   | 4 | 5.6 | 4 | 4 | 3 | 4 | 4 | 4 | 3 | 1 | 2 | 3 | 4 |
| II | 4 | 11.2 | 2 | 3 | 3 | 3 | 3 | 2 | 3 | 3 | 3 | 3 | 4 |
|   | 4 | 5.6 | 1 | 3 | 1 | 2 | 3 | 1 | 2 | 1 | 4 | 1 | 2 |
| III | 4 | 11.2 | — | 3 | 3 | 2 | 4 | — | 2 | 3 | 4 | 3 | 4 |
|   | 4 | 5.6 | — | 3 | 3 | 2 | 4 | — | 2 | 1 | 4 | 1 | 3 |
| IV | 4 | 11.2 | — | 2 | 3 | 2 | 4 | — | 2 | 2 | 3 | 3 | 3 |
|   | 4 | 5.6 | — | 2 | 3 | 2 | 4 | — | 2 | 1 | 4 | 3 | 3 |
| V | 4 | 11.2 | — | 4 | 2 | 2 | 4 | 4 | 2 | 0 | 3 | 2 | 3 |
|   | 4 | 5.6 | — | 3 | 1 | 1 | 4 | 3 | 1 | 1 | 1 | 1 | 2 |

TABLE II

| Compound of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| I | 4 | 5.6 | 2 | 3 | 2 | 3 | 3 | 4 | 4 | 3 | 2 | 4 | 3 | 3 | 3 | 3 | 3 | 4 |
|   | 4 | 1.12 | 1 | 1 | 1 | 0 | 2 | 3 | 2 | 2 | 2 | 3 | 2 | 2 | 1 | 1 | 1 | 2 |
|   | 2 | 0.28 | 0 | 0 | 0 | 0 | 0 | 1 | 0 | 0 | 0 | 0 | 0 | 0 | 0 | 0 | 2 | 1 |
|   | 2 | 0.056 | 0 | 0 | 0 | 0 | 0 | 0 | 0 | 0 | 0 | 0 | 0 | 0 | 0 | 0 | 0 | 0 |
| II | 4 | 5.6 | 3 | 2 | 2 | 3 | 3 | 4 | 3 | 3 | 3 | 4 | 3 | 3 | 3 | 4 | 3 | 4 |
|   | 4 | 1.12 | 1 | 1 | 0 | 2 | 1 | 4 | 1 | 0 | 0 | 3 | 1 | 1 | 0 | 3 | 2 | 2 |
|   | 4 | 0.28 | 0 | 0 | 0 | 0 | 0 | 0 | 0 | 0 | 2 | 1 | 0 | 0 | 0 | 0 | 0 | 0 |
|   | 2 | 0.056 | 0 | 0 | 0 | 0 | 0 | 0 | 0 | 0 | 0 | 0 | 0 | 0 | 0 | 0 | 0 | 0 |

EXAMPLE IX

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
| --- | --- |
| 0–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | Plant Species | | | | | | | | | | |
| --- | --- | --- | --- | --- | --- | --- | --- | --- | --- | --- | --- | --- | --- |
| | | | A | B | C | D | E | F | G | H | I | J | K |
| I | 2 | 11.2 | 3 | 0 | 1 | 2 | 1 | 1 | 1 | 2 | 3 | 1 | 3 |
| II | 2 | 11.2 | 3 | 0 | 1 | 1 | 2 | 1 | 0 | 2 | 3 | 0 | 1 |
| III | 2 | 11.2 | — | 0 | 0 | 0 | 2 | — | 1 | 1 | 1 | 0 | 0 |
| IV | 2 | 11.2 | — | 0 | 0 | 0 | 3 | 0 | 1 | 2 | 1 | 0 | 0 |
| V | 2 | 11.2 | — | 1 | 0 | 0 | 2 | 0 | 0 | 0 | 0 | 0 | 0 |

TABLE IV

| Compound of Example No. | WAT | kg/h | Plant Species | | | | | | | | | | | | | | |
| --- | --- | --- | --- | --- | --- | --- | --- | --- | --- | --- | --- | --- | --- | --- | --- | --- |
| | | | L | M | N | O | P | B | Q | D | R | E | F | C | J | S | K | T |
| I | 2 | 11.2 | 3 | 3 | 0 | 0 | 0 | 0 | 3 | 2 | 3 | 3 | 3 | 2 | 1 | 1 | 1 | 3 |
| | 2 | 5.6 | 1 | 1 | 0 | 0 | 0 | 0 | 2 | 0 | 0 | 0 | 2 | 0 | 0 | 0 | 0 | 2 |
| | 2 | 1.12 | 0 | 0 | 0 | 0 | 0 | 0 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, al parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3–4, "The Recirculating Sprayer and Roundup Herbicide", Derting, Claude W., pp. 5–7, and "C. D. A. Herbicide Application", McGarvey, Frank X., *Weeds Today*, Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises contacting said plants or plant growth medium with a herbicidal amount of a compound of the formula

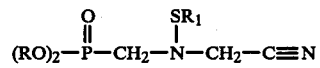

wherein R is phenyl, naphthyl or biphenylyl or phenyl, naphthyl or biphenylyl substituted with from one to three substituents independently selected from the class consisting of lower alkyl, lower alkoxy, lower alkylthio, lower alkoxycarbonyl, methylenedioxy, trifluoromethyl, cyano, nitro and halogen; and $R_1$ is alkyl or cycloalkyl.

2. A method according to claim 1 wherein R is phenyl.

3. A method according to claim 2 wherein said compound is phosphonic acid, (((cyanomethyl)methylthio)amino)methyl)-, diphenyl ester.

4. A method according to claim 2 wherein the compound is phosphonic acid, (((cyanomethyl)ethylthio)amino)methyl)-, diphenyl ester.

5. A method according to claim 2 wherein the compound is phosphonic acid, (((cyanomethylisopropylthio)amino)methyl)-, diphenyl ester.

6. A method according to claim 2 wherein the compound is phosphonic acid, (((cyanomethyl)(cyclohexylthio)amino)methyl)-, diphenyl ester.

7. A method according to claim 2 wherein said compound is phosphonic acid, (((cyanomethyl)n-butylthio)amino)methyl)-diphenyl ester.

8. A compound of the formula

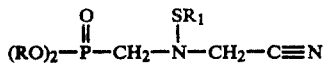

wherein R is phenyl, naphthyl or biphenylyl or phenyl, naphthyl or biphenylyl substituted with from one to three substituents independently selected from the class consisting of lower alkyl, lower alkoxy, lower alkylthio, lower alkoxycarbonyl, methylenedioxy, trifluoromethyl, cyano, nitro and halogen; and $R_1$ is alkyl or cycloalkyl.

9. A compound according to claim 8 wherein R is phenyl.

10. A compound according to claim 9 wherein said compound is phosphonic acid, (((cyanomethyl)methylthio)amino)methyl)-, diphenyl ester.

11. A compound according to claim 9 wherein the compound is phosphonic acid, (((cyanomethyl)ethylthio)amino)methyl)-, diphenyl ester.

12. A compound according to claim 9 wherein the compound is phosphonic acid, (((cyanomethyl)isopropylthio)amino)methyl)-, diphenyl ester.

13. A compound according to claim 9 wherein the compound is phosphonic acid, (((cyanomethyl)(cyclohexylthio)amino)methyl)-, diphenyl ester.

14. A compound according to claim 9 wherein said compound is phosphonic acid (((cyanomethyl)(n-butylthio)amino)methyl)-diphenyl ester.

15. A herbicidal composition comprising an inert adjuvant and a herbicidally effective amount of a compound of the formula

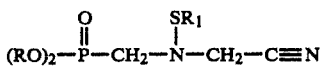

wherein R is phenyl, naphthyl or biphenylyl or phenyl, naphthyl or biphenylyl substituted with from one to three substituents independently selected from the class consisting of lower alkyl, lower alkoxy, lower alkylthio, lower alkoxycarbonyl, methylenedioxy, trifluoromethyl, cyano, nitro and halogen; and $R_1$ is alkyl or cycloalkyl.

16. A composition according to claim 15 wherein R is phenyl.

17. A composition according to claim 16 wherein said compound is phosphonic acid, (((cyanomethyl)methylthio)amino)methyl)-, diphenyl ester.

18. A composition according to claim 16 wherein the compound is phosphonic acid, (((cyanomethyl)ethylthio)amino)methyl)-, diphenyl ester.

19. A composition according to claim 16 wherein the compound is phosphonic acid, (((cyanomethyl)isopropylthio)amino)methyl)-, diphenyl ester.

20. A composition according to claim 16 wherein the compound is phosphonic acid, (((cyanomethyl)(cyclohexylthio)amino)methyl)-, diphenyl ester.

21. A composition according to claim 16 wherein said compound is phosphonic acid (((cyanomethyl)(n-butylthio)amino)methyl)-diphenyl ester.

* * * * *

UNITED STATES PATENT AND TRADEMARK OFFICE
CERTIFICATE OF CORRECTION

PATENT NO. : 4,445,929

DATED : May 1, 1984

INVENTOR(S) : James A. Sikorski and Mary A. Hoobler

It is certified that error appears in the above-identified patent and that said Letters Patent is hereby corrected as shown below:

Column 7, line 62: "al" should be --all--

Column 10, line 21: "Roundup" should be --Roundup®--

Signed and Sealed this

Twentieth Day of November 1984

[SEAL]

Attest:

GERALD J. MOSSINGHOFF

Attesting Officer

Commissioner of Patents and Trademarks